US008977359B2

(12) United States Patent
Rossing

(10) Patent No.: US 8,977,359 B2
(45) Date of Patent: *Mar. 10, 2015

(54) SYSTEM FOR SETTING PROGRAMMABLE PARAMETERS FOR AN IMPLANTABLE HYPERTENSION TREATMENT DEVICE

(71) Applicant: CVRx, Inc., Minneapolis, MN (US)

(72) Inventor: Martin A. Rossing, Coon Rapids, MN (US)

(73) Assignee: CVRx, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/263,579

(22) Filed: Apr. 28, 2014

(65) Prior Publication Data

US 2014/0236256 A1    Aug. 21, 2014

Related U.S. Application Data

(63) Continuation of application No. 11/254,042, filed on Oct. 18, 2005, now Pat. No. 8,712,522.

(51) Int. Cl.
*A61N 1/18*    (2006.01)
*A61N 1/36*    (2006.01)
(Continued)

(52) U.S. Cl.
CPC ............... *A61N 1/36139* (2013.01); *A61N 1/08* (2013.01); *A61N 1/36114* (2013.01); *A61N 1/36117* (2013.01); *A61N 1/37* (2013.01); *A61N 1/37247* (2013.01)
USPC .......................................................... 607/23

(58) Field of Classification Search
USPC .................. 607/2, 4, 5, 9, 23, 30, 32, 44, 60; 128/899, 903
See application file for complete search history.

(56) References Cited

U.S. PATENT DOCUMENTS 3,650,277 A     3/1972   Sjostrand et al.
4,080,966 A     3/1978   McNally et al.
(Continued)

FOREIGN PATENT DOCUMENTS

WO     WO 03/034916     5/2003

OTHER PUBLICATIONS

International Preliminary Report on Patentability from related PCT Application PCT/US2006/039073, dated Apr. 23, 2008, 8 pgs.
(Continued)

*Primary Examiner* — Allen Porter, Jr.
(74) *Attorney, Agent, or Firm* — Patterson Thuente Pedersen, P.A.

(57) ABSTRACT

A real time, heart rate monitor and a hemodynamic monitoring system are operably integrated with the programmer system for an implantable hypertension treatment device. A series of tests are automatically performed to set programmable parameters for the implantable hypertension treatment device without clinician intervention. In one embodiment, a predetermined level of a dose-response evaluation is initiated for each test in the series. Preferably, the programmer system monitors the heart rate to determine whether a hemodynamic measurement should be initiated at all for a given test, as well as whether the hemodynamic measurement should be initiated earlier or later than a predetermined settling period for assessing the sympathetic nervous response to the test dose. In one embodiment, this determination is based on heart rate stability/instability. Alternatively, other indicators of sympathetic/parasympathetic tone, such as heart rate variability, may be used to trigger/delay the timing of the hemodynamic measurement.

20 Claims, 12 Drawing Sheets

(51) Int. Cl.
*A61N 1/37* (2006.01)
*A61N 1/372* (2006.01)
*A61N 1/08* (2006.01)

(56) References Cited

U.S. PATENT DOCUMENTS

| | | | |
|---|---|---|---|
| 4,967,749 | A | 11/1990 | Cohen |
| 5,320,643 | A | 6/1994 | Roline et al. |
| 5,487,752 | A | 1/1996 | Salo et al. |
| 5,707,400 | A | 1/1998 | Terry, Jr. et al. |
| 5,733,259 | A | 3/1998 | Valcke et al. |
| 5,749,900 | A | 5/1998 | Schroeppel et al. |
| 6,311,089 | B1 | 10/2001 | Mann et al. |
| 6,371,922 | B1 | 4/2002 | Baumann et al. |
| 6,463,325 | B1 | 10/2002 | Bolz |
| 6,522,926 | B1 | 2/2003 | Kieval et al. |
| 6,587,723 | B1 | 7/2003 | Sloman et al. |
| 6,735,479 | B2 | 5/2004 | Fabian et al. |
| 7,047,071 | B2 | 5/2006 | Wagner et al. |
| 8,712,522 | B1 | 4/2014 | Rossing |
| 2004/0011366 | A1 | 1/2004 | Schulman et al. |
| 2005/0149143 | A1 | 7/2005 | Libbus et al. |
| 2006/0089678 | A1 | 4/2006 | Shalev et al. |

OTHER PUBLICATIONS

International Search Report from related PCT Application PCT/US2006/039073, dated Sep. 19, 2007, 2 pgs.
Schmidli, J., et al. "Response to Acute Electrical Activation of the Carotid Baroreflex is Maintained in Drug Refractory Hypertension". Journal of Hypertension, vol. 23, Supplemental 2, Jun. 2005, 1 pg.
Application and File History for U.S. Appl. No. 11/254,042, filed Oct. 18, 2005. Inventor: Martin A. Rossing.

SYSTEM FOR SETTING PROGRAMMABLE PARAMETERS FOR AN IMPLANTABLE HYPERTENSION TREATMENT DEVICE

RELATED APPLICATION

This application is a continuation of U.S. application Ser. No. 11/254,042 filed Oct. 18, 2005, now issued as U.S. Pat. No. 8,712,522, the disclosure of which is hereby incorporated by reference in its entirety.

BACKGROUND OF THE INVENTION

Field of the Invention

The present invention relates generally to electrical therapeutic systems for hypertension treatment. More particularly, the present invention relates to methods and apparatus for setting programmable parameters for an implantable hypertension treatment device.

Implantable devices for treating high blood pressure or hypertension by stimulating various nerves and tissue in the body are known and described, for example, in U.S. Pat. No. 3,650,277 (stimulation of carotid sinus nerve), U.S. Pat. No. 5,707,400 (stimulation of vagal nerve), and U.S. Pat. No. 6,522,926 (stimulation of baroreceptors). While many aspects of these implantable devices are similar to implantable devices used to treat cardiac arrhythmias, such as pacemakers and implantable defibrillators, there are significant differences in the application and operation of implantable hypertension devices due to the fact that the slower responding baroreflex system is being stimulated, instead of the rapid response of cardiac stimulation used for pacemakers.

Implantable electronic medical devices typically require post-implantation programming of certain parameter values in order to establish proper patient-specific performance. For example, implantable cardiac stimulation devices, such as pacemakers and implantable cardiac defibrillators (ICDs) utilize a threshold margin testing procedure in which the level of electrotherapy pulses is established for the specific patient. Each patient will have a unique tissue impedance and susceptibility to the electrotherapy signaling, and the configuration of electrodes can produce different results for the same stimulation pulse. As a result, it is necessary to program certain parameter values in the pacemaker or ICD to establish optimum therapy for that patient for a particular implantable device and electrode configuration.

In the case of a conventional pacemaker, the object of such parameter programming is to establish the voltage level of the pacing pulses such that the pulses are of a sufficiently high amplitude to achieve reliable capture of the patient's heart while being of a minimal amplitude to achieve the desired therapy to provide the longest possible battery life for the device. Similarly, in the case of implantable defibrillators, the defibrillation pulse amplitude is set to the minimal level to achieve reliable electrotherapy with minimal tissue damage and maximum battery life. In each case, the programmable parameters are typically set at some safety threshold margin above the measured pacing capture or defibrillation threshold values.

Automatic systems for testing and configuring the threshold parameters of implantable cardiac stimulation devices are described, for example, in U.S. Pat. Nos. 5,320,643, 5,487,752 and 6,311,089. Examples of implantable cardiac stimulation devices that automatically self-configure the operating parameters for the device using built-in measurement/circuitry and sensors and some type of configuration algorithm are described in U.S. Pat. Nos. 6,463,325 and 6,587,723. U.S. Pat. No. 6,371,922 describes optimizing cardiac stimulation pulses delivered by a pacemaker based on measuring Baroreflex sensitivity.

A common aspect to these conventional automatic device configuring systems for implantable cardiac stimulation devices is that the physiological response of the patient is generally readily observable a short time (on the order of seconds) following an administration of electrotherapy by the implantable device. Another common aspect is that the physiological response of cardiac stimulation is generally binary in nature. Stated another way, the desired physiological response is either present or absent. In the case of a pacemaker, the pacing pulse for the heart is either captured or not captured; in the case of a defibrillator, the cardiac rhythm is either restored, or not restored. Detecting the presence or absence of these fast and easily discernable physiological responses to the electrotherapy signals applied to the autonomic nervous system is therefore a relatively straight-forward endeavor. Furthermore adjustment of the electrotherapy signaling to optimize device performance in response to the physiological responses (or lack thereof) can be done incrementally in a relatively short period of time.

By contrast, implantable devices for treating hypertension by regulating blood pressure in a patient may induce a physiological effect in the sympathetic nervous system that is not binary in nature and that tends to be protracted or sustained. For example, baroreceptor stimulation effects an incremental, or gradual, change in blood pressure that is observable only after a relatively longer period of time (on the order of minutes). Therefore, conventional automatic device configuration systems and methods developed for implantable cardiac stimulation devices are not directly applicable for configuring hypertension treatment devices.

Presently, hypertension treatment devices are configured based on monitoring performed manually by clinical personnel. This process of dose-response testing for a hypertension treatment devices requires the clinical personnel to have an instrument for taking blood pressure measurement of the patient, such as an automated blood pressure measurement system like the Dynamap® blood pressure system. In addition, the patient's heart rate must be monitored to insure that the heart rate does not drop to a lower than desired value. Therefore, the patient is also connected to a real time, or continuous, heart rate monitor, such as a surface ECG or $SP0_2$ measurement device. Finally, the clinical personnel must manually operate the programmer for the implantable hypertension treatment device to repeatedly perform the testing routine that typically includes: (a) programming the implantable hypertension treatment device, (b) monitoring the heart rate while waiting a prescribed number of minutes to take initiate measurement of the hemodynamic parameters of the patient, (c) manually starting the measurement of the hemodynamic parameters of the patient, (d) manually recording the results of the hemodynamic parameters of the patient and correlating those results to the programmed settings, (e) determining if the recorded results indicate whether the dose-response has stabilized, and (f) if not, continue repeating the test process at the next higher dose response level. Presently, all of these instruments are separate from the programmer and require separate monitoring and operation from the programmer device.

When configuring an implanted hypertension treatment device by this kind of dose-response test process, the clinical personnel must keep track of issues such as the time until a physiological response to a change in electrotherapy administration, operation of the device programmer, operation of the blood pressure measuring apparatus, recording measurements, and correlating measurements with the most recent electrotherapy set point, all while continuously monitoring the safety of the patient during the procedure by keeping track of the patient's heart rate. Because such procedures are operator intensive, subject to measurement variability, and time-consuming, there are significant drawbacks to the current methods for configuring implanted blood pressure regulating devices.

BRIEF SUMMARY OF THE INVENTION

The present invention is a system for automating the setting of programmable parameters for an implantable hypertension treatment device. One aspect of the present invention integrates a real time heart rate monitor and a hemodynamic monitoring system with the programmer system for an implantable hypertension treatment device. A series of tests are automatically performed to set programmable parameters for the implantable hypertension treatment device under program control that permits automatic operation without clinician intervention. In one embodiment, a predetermined level of a dose-response evaluation is initiated for each test in the series. Preferably, the programmer system monitors the heart rate to determine whether a hemodynamic measurement should be initiated at all for a given test, as well as whether the hemodynamic measurement should be initiated earlier or later than a predetermined settling period for assessing the sympathetic nervous response to the test dose. In one embodiment, this determination is based on heart rate stability/instability. Alternatively, other indicators of sympathetic/parasympathetic tone, such as heart rate variability, may be used to trigger/delay the timing of the hemodynamic measurement.

In one embodiment, the heart rate monitor and hemodynamic measurement system are separate devices in communication with the programmer system. In another embodiment, the heart rate monitor and hemodynamic measurement system are incorporated into the programmer system. In another embodiment, the hemodynamic measurement system and/or the heart rate monitor system may be integrated with the implantable hypertension treatment device that is in communication with the programmer. In a further embodiment, the hemodynamic measurement system and/or the heart rate monitor system may be implanted separately from the implantable hypertension device and could be in communication with the programmer, either directly or via the implantable hypertension device.

The present invention avoids errors that can be associated with the existing manual testing procedures for setting programmable parameters for implantable hypertension treatment devices. The present invention also permits the testing to be performed more rapidly and with minimal clinician intervention during the procedure. The integration of the programmer system in accordance with the present invention improves the overall safety of the test procedure as the system can more rapidly detect and respond to a low heart rate condition than manual monitoring and intervention.

Unlike the prior art testing techniques for setting programmable parameters for implantable cardiac stimulation devices, the dose-response characteristics associated with an implantable hypertension treatment device are much more linear in that the hemodynamic response of various programmed conditions needs to be measured in order to determine an algorithm or model of the response. The clinician may use the output of this model to guide the clinician in programming the parameters of the implantable hypertension treatment device so that the desired hemodynamic response is achieved. The dose response procedure of the present invention also takes significantly more time than, for example, the pacemaker threshold margin test, because the hemodynamic response to certain programmed conditions may initiate a response nearly immediately after programming, or it may take several minutes for the patient to achieve a stabilized response.

Preferably, the clinician monitors the test procedure from a remote viewing/monitoring location. In one embodiment, the programming system includes a remote control to facilitate the remote monitoring of the test procedure. Preferably, the remote control would be connected with the programming system by a wireless connection, such as RF, infrared or optical, although it will be recognized that the remote control could also be provided with a wired connection. The present invention recognizes that even modest amounts of interaction or talking with a clinician can cause a change in the blood pressure of the patient, thereby affecting the results of the test procedure. The automated nature and integration of the present invention permits the clinician to avoid interaction with the patient during the test procedure so as to minimize the chances of inadvertently affecting the results of the test procedure.

In one embodiment, the hemodynamic measurement system may be a discontinuous or non-real time measurement system, such as an inflated/deflated cuff where measurements are taken periodically rather than continuously. Alternatively, a real-time waveform measurement system, such as a Finometer™ blood pressure instrument manufactured by Finapres® or continuous pressure monitor, may be utilized. In the embodiment in which a real-time waveform measurement system is used, the hemodynamic measurement system may be used in place of the heart rate monitor, or to augment the heart rate monitor, in terms of the assessment of whether a stable response has been achieved for a given dose-response test.

The present invention enables automated and faster integration of data from the test results, and in one embodiment graphic display of the test results, to assist the clinician in determining the desired parameters for the implantable hypertension treatment device. In this embodiment, the programmer system and/or the implantable hypertension treatment device include data storage for storing dose response characteristics, preferably including historical dose response characteristics for the given patient. These dose response characteristics may be displayed to the clinician for diagnostic purposes, as well as for setting the programmable parameters for the implantable hypertension treatment device. In another embodiment, the historical data may also be used to shorten up the test period for the series of dose-response tests. For example, if past data has reasonably determined the response threshold and response slope, a new threshold and slope may be determined with few test conditions by, for example, using the previous threshold and response slope to interpolate among fewer dose response test points.

DETAILED DESCRIPTION OF THE INVENTION

Figure 1:
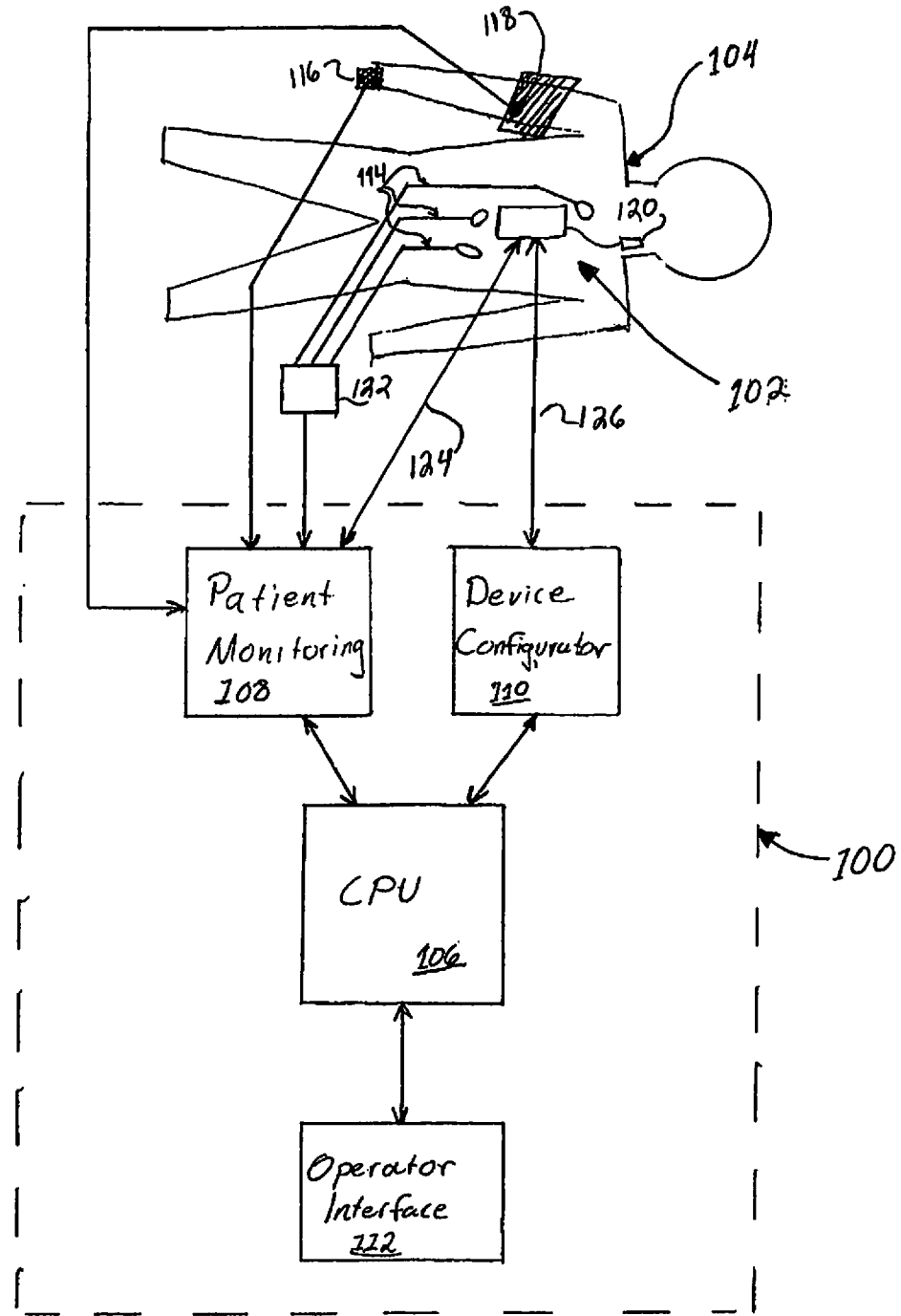
FIG. 1 is an overview block diagram illustrating a programming system in accordance with one aspect of the present invention interfaced with a patient and with a hypertension treatment device implanted in the patient.

FIG. 1 is a schematic diagram illustrating a programmer system 100 for a hypertension treatment device 102 implanted in patient 104. Programmer system 100 is generally adapted to automatically conduct dose-response testing in the patient using the treatment device 102, and to optionally determine a suitable operating point or calibration curve for the treatment device 102 based on the dose-response testing and program the implanted treatment device 102 accordingly.

Programmer system 100 includes a CPU 106 that is configured with machine-readable instructions to execute its operating functions. CPU 106 is communicatively coupled with a patient monitoring sub-system 108, a device configurator sub-system 110, and operator interface sub-system 112. The communicative coupling can include any suitable arrangement for the exchange of data, control, and other such communication between the aforementioned sub-systems of programmer system 100, including a data bus, serial communications, analog signaling, wireless communications, and the like, and combinations thereof.

In one type of embodiment, the CPU 106, patient monitoring sub-system 108, device configurator sub-system 110, and operator interface 112 are closely integrated into a single device or system. In other types of embodiments, one or more of these sub-systems is implemented as a separate device that is operatively interfaced into the overall system, but not necessarily fully controlled by CPU 106. In one such embodiment, for example, one or more sub-systems have their own CPU (not shown) configured to control only the associated sub-system, and only an exchange of data takes place between loosely-integrated sub-systems (i.e., no control or configuration information is exchanged). Persons skilled in the art will recognize that, for one or more of these sub-systems, any degree of integration into the greater system is within the spirit of the invention.

Patient monitoring subsystem 108 reads one or more sensors configured to observe the physiological condition of patient 104. Preferably, patient monitoring sub-system 108 reads at least the patient's hemodynamic condition. Examples of sensors suitable for taking these measurements include electrocardiogram (EKG) sensors 114, pulse oximetry sensor 116, cuff-type blood pressure sensor 118, and implanted blood pressure sensor 120. Additionally, hemodynamic monitoring can include cardiovascular resistance information and sympathetic/parasympathetic tome information (not shown). Sensors can be discontinuous, or non-real-time, such as a cuff-type blood pressure measuring device. Sensors can also be of the continuous type, such as a Finometer™ blood pressure instrument manufactured by Finapres®. As illustrated, the implanted blood pressure sensor 120 can be a part of implanted treatment device 102. Similarly, the implanted treatment device can include other hemodynamic sensors, such as a heartbeat sensor (not shown) or blood oxygenation sensor (not shown). Patient monitoring subsystem 108 is interfaced with each of the respective sensors via suitable hardware. For example, in one embodiment, patient monitoring subsystem 108 is connected to the EKG sensors via an EKG system 122. In one embodiment, patient monitoring subsystem 108 receives information based on a sensed condition by the implanted treatment device 102 via communication channel 124. Communication channel 124 can be over any suitable communications media, including via conductive material, via electromagnetic radiation (heat, light, radio, etc.), via mechanical signaling such as ultrasonic transduction, and the like. In one embodiment, communication channel 124 is common with communication channel 126 between implanted device 102 and device configurator sub-system 110.

Patient monitoring subsystem 108 monitors one or more of these sensors, or other suitable sensors (and supplies electrical power, air pressure, or other appropriate enablement needed to facilitate operation of the sensors), converts each sensor's reading into a form suitable for reading by the CPU, and communicates the sensor information to the CPU according to the established communications protocol.

Device configurator sub-system 110 includes hardware and/or software for communicating with implanted treatment device 102 over communication channel 126. Communications over channel 126 include device configurator sub-system 110 reading status, data, and other relevant information originating in the treatment device 102, and transmitting configuration information, calibration, or instructions to the treatment device 102. Communication channel 126 can be over any suitable communications media, including via conductive material, via electromagnetic radiation (heat, light, radio, etc.), via mechanical signaling such as ultrasonic transduction, and the like.

Operator interface 112 permits a human user of system 100, such as a clinician, to observe the operation of system 100, including monitoring the patient's sensed condition, the activity of implanted treatment device 102, and the progress of programming the treatment device 102. In one embodiment, information is displayed to the clinician in a graphical format, such as time-based rolling plots of selected patient conditions, together with the progress of the dose-response testing. Such a display, which includes providing stored historic dose-response data of the patient, can enable the clinician to readily identify any particular trends in the dose-response test results.

In a preferred type of embodiment, operator interface 112 also enables the clinician to manually control the dose-response testing, determination of operating point for implanted device 102, and/or the programming of the implanted device 102 to a selectable extent. In one example embodiment of this type, an operator has the option of running the system 100 in a fully automatic mode, or exercising some level of control over patient monitoring, dose-response testing, analysis of the dose-response testing results, or configuring of the implanted device 102. In one embodiment, operator interface 112 is configured to accept manually inputted data representing a condition of the patient for incorporation into the analysis of the dose-response testing.

Operator interface 112 can be integrated closely with one or more sub-systems of system 100 such that CPU 106 controls operator interface 112. Alternatively, operator interface 112 can itself be a separate device that merely exchanges data with CPU 106. In this latter embodiment, operator interface 112 can be implemented in a personal computer (PC) running an application program that enables the PC to interface with CPU 106 and facilitate the user display and inputs. In one embodiment, operator interface 112 can be interfaced with CPU 106 over a computer network. Preferably, operator interface 112 is situated remotely from the patient to minimize the undesirable effect on the accuracy of measurement of the patient's condition resulting from interaction between the clinician and patient.

Figure 2:
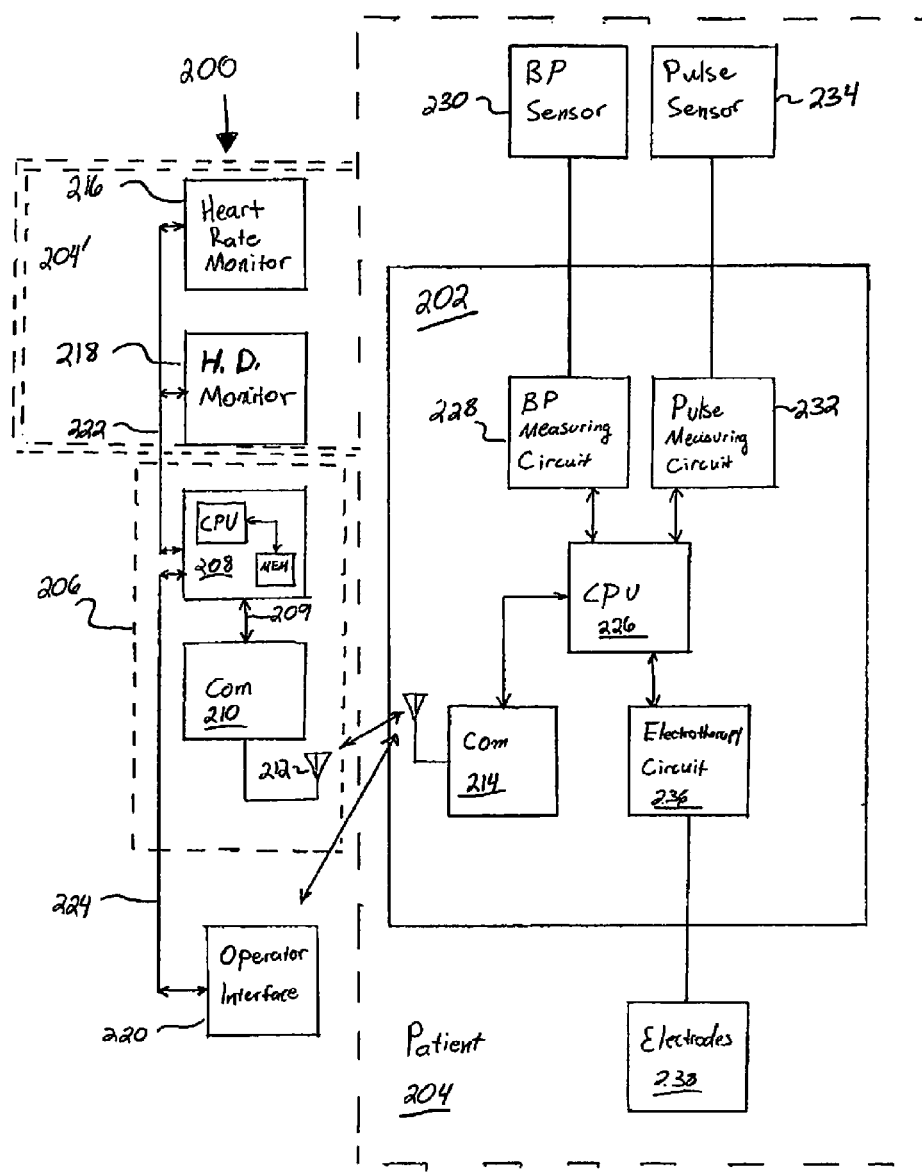
FIG. 2 is a schematic diagram illustrating an exemplary arrangement of programming system components and their interface with one another and with an hypertension treatment device implanted in a patient.

FIG. 2 illustrates an exemplary arrangement of components of a programming system 200 and their interface with one another and with a hypertension treatment device 202 implanted in a patient 204. Programming system 200 includes a programmer 206, which has processor 208 interfaced with communications circuit 210 via interface 209 between processor 208 and communications circuit 210 can be a PCI bus, I2C bus, or any other suitable interface known in the art. Processor 208 includes at least a CPU core and memory MEM. Communications circuit 210 includes transceiver circuitry coupled with an antenna 212 for communicating with communications circuit 214 of implanted hypertension treatment device 202.

Programming system 202 further includes heart rate monitor 216 and hemodynamic monitor 218. As illustrated in FIG. 2, these components are interfaced with processor 208 via bus 222, which can be the same interface as interface 209, or another suitable interface known in the art. Heart rate monitor 216 and hemodynamic monitor 218 are each operatively interfaced with the patient 204 to measure the patient's physiological conditions, as represented by the double-dashed lines and indicated at 204'.

Operator interface 220 is operatively coupled with processor 208 via interface bus 224. Interface bus 224 can be the same interface as interface 222, or can be another suitable interface.

Implanted hypertension treatment device 202 includes CPU 226 that is configured to control the operation of the device. CPU 226 can detect the need for applying electrotherapy via patient monitoring circuitry that includes blood pressure measuring circuit 228 interfaced with implanted blood pressure sensor 230, and via pulse measuring circuit 232 interfaced with implanted pulse sensor 234. CPU 226 is further configured to administer the electrotherapy via electrotherapy circuit 236 and electrodes 238.

Heart rate monitor 216 and hemodynamic monitor 218 are interfaced with the exterior of the patient. In another type of embodiment, heart rate monitor 216 and hemodynamic monitor 218 are implanted in the patient and include data gathering and communication electronics for acquiring the patient's physiological conditions and transmitting data representing the same to CPU 208 via communications circuit 210. In this type of embodiment, heart rate monitor 216 and hemodynamic monitor 218 can either operate independently of implanted hypertension treatment device 202, or can communicate information to the treatment device 202.

In operation, programming system 200, according to one embodiment, can verify that heart rate monitor 216 and hemodynamic monitor 218 provide substantially similar indicia of the patient's physiological state as provided via blood pressure measuring circuit 228 and pulse measuring circuit 232. If these indicia are dissimilar to an unacceptable degree, programming system 200 can calibrate the measuring circuits 228 and 232 of implanted device 202, or the implanted device's interpretation of the measurement data generated by the measuring circuits 228 and 232. Programming system 200 is further configured to conduct a set of dose-response tests by commanding implanted device 202 to systematically vary the therapy dosage over time, while monitoring the effect of the therapy on the patient's physiology via at least one of heart rate monitor 216, hemodynamic monitor 218, blood pressure measuring circuit 228, and/or pulse measuring circuit 232. As will be discussed in detail below, one aspect of the invention is directed to the use of pulse, or heart rate measurement in lieu of hemodynamic or blood pressure measurement to reduce the time needed to conduct each dose-response test.

Figure 3A:
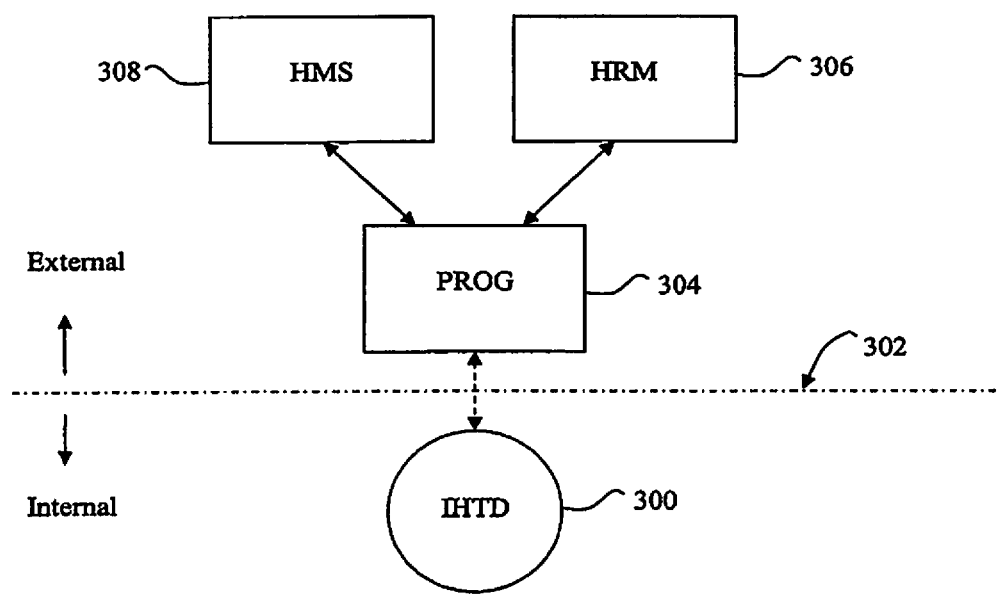
FIGS. 3A-3D are block diagrams illustrating various examples of arrangements between a programming system, patient monitors, and an implanted hypertension treatment device within the spirit of the invention.

FIGS. 3A-3D illustrate various examples of measurement arrangements for monitoring the patient's physiology during the dose-response testing. In FIG. 3A, implanted hypertension treatment device (IHTD) 300 is situated on the internal side of patient boundary 302. Programmer 304 is communicatively coupled with IHTD 300. Heart rate monitor (HRM) 306 and hemodynamic monitoring system (HMS) 308 are operably coupled to programmer 304 and, during system operation, are physically engaged with the patient's exterior. In one embodiment, one or both of HRM 306 and HMS 308 are integrated with the programmer 304. In another embodiment, at least one of HRM 306 and HMS 308 are separate devices electrically interconnected with programmer 304.

Figure 3B:
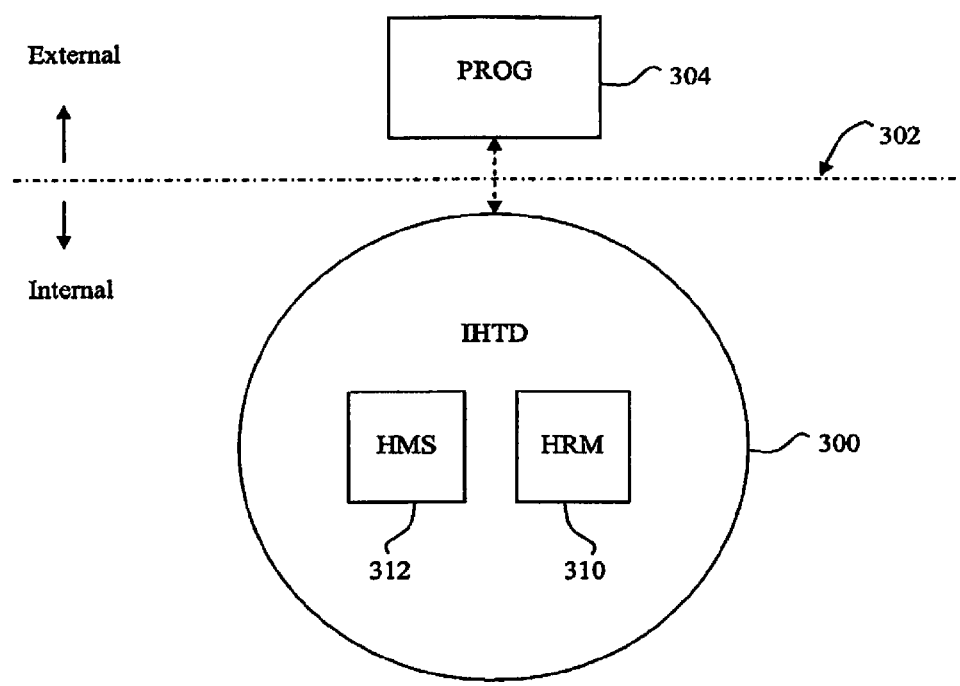

In FIG. 3B, heart rate monitor HRM 310 and hemodynamic monitoring system 312 are implanted in the patient as part of IHTD 300. Programmer 304 receives patient physiology information from one or both of HRM 310 and/or HMS 312, which information is collected and analyzed during the dose-response testing. In this embodiment, additional external heart rate monitoring or hemodynamic monitoring is avoided.

Figure 3C:
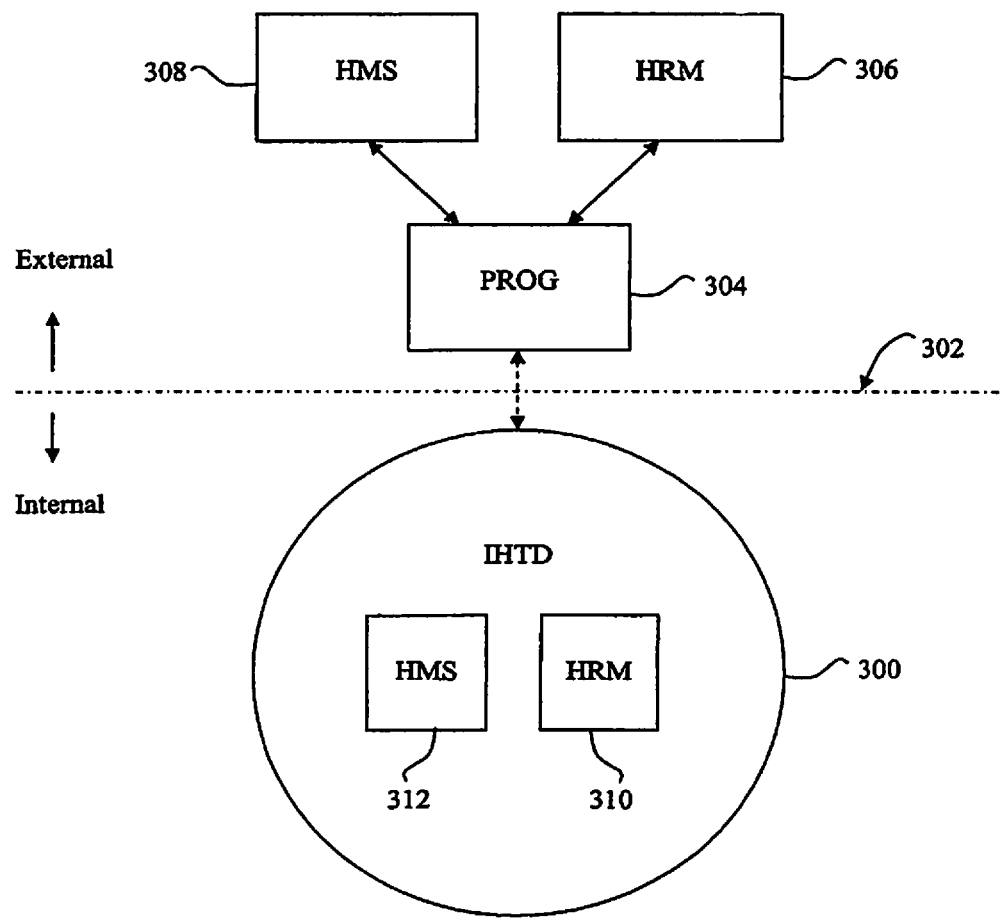

By contrast, the example arrangement of FIG. 3C has external heart rate monitoring and hemodynamic monitoring facilitated respectively by HRM 306 and HMS 308. This arrangement is similar to the arrangement described above with reference to FIG. 2. One advantage of having available externally-measured physiology information in addition to 30 internally-measured physiology information by the IHTD is the externally-measured condition of the patient can be used by the programmer 304 verify accuracy of the internally-measured condition. In one embodiment, programmer 304 calibrates the measurements of internal HRM 310 and HMS 312.

In another embodiment, programmer 304 configures IHTD 300 to supply therapy dosage based on the internally-measured physiology data by HRM 310 and HMS 312 irrespective of whether these measurements are accurate relative to the externally-measured physiologic condition of the patient by external HRM 306 and HMS 308. The calibration of IHTD 300 achieved through the dose response testing carried out by programmer 304 correlates the physiology information obtained from internal measurements with those obtained from the external measurements. Assuming, for example, that the external measurements obtained by HRM 306 and HMS 308 are an accurate representation of the patient's actual condition, programmer 304 will establish the appropriate therapy dosage based on the externally-obtained physiology information. After calibration, the IHTD 300 will administer the established therapy dosage according to physiologic measurements made by internal monitors HRM 310 and HMS 312, which represent the patient's actual condition 15 to IHTD 300.

Figure 3D:
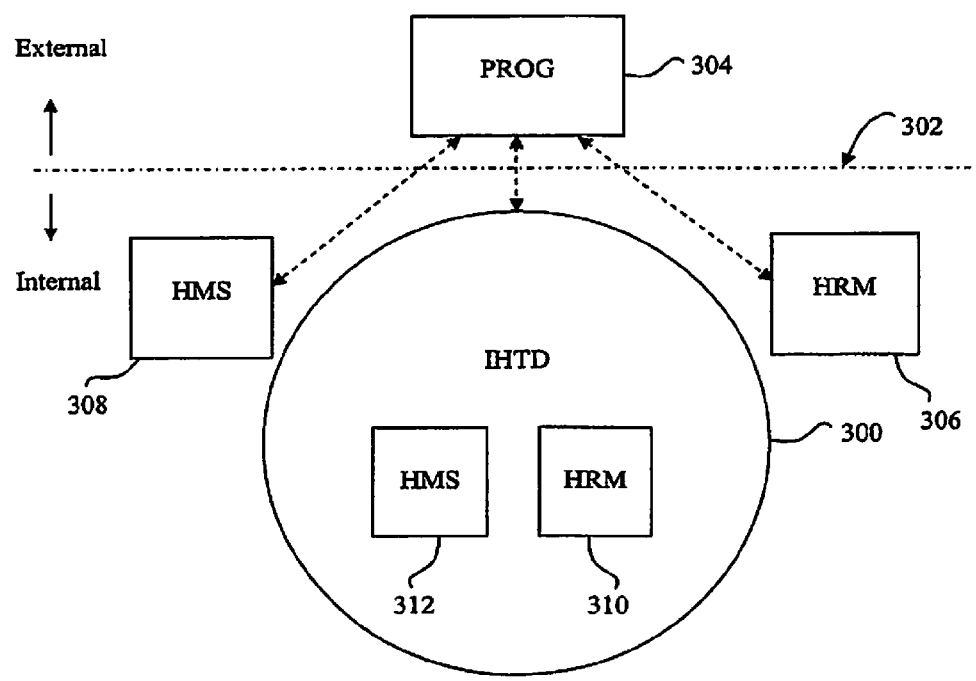

The example arrangement illustrated in FIG. 3D is similar to the arrangement of FIG. 3C in that programmer 304 gathers patient physiology data from HRM 306 and HMS 308 that are separate from HRM 310 and HMS 312 integral to IHTD 300. However, in the arrangement of FIG. 3D, HRM 306 and HMS 308 are implanted in the patient and communicatively coupled to programmer 304 through patient boundary 302.

Persons skilled in the relevant arts will appreciate that variations and combinations of the example embodiments of FIGS. 3A-3D are all within the spirit of the invention. Thus, referring to FIGS. 3C and 3D for example, HRM 306 can be implanted in the patient as depicted in FIG. 3D, while HMS 308 can be external to the patient, as depicted in FIG. 3C. 25 Persons skilled in the art will also appreciate that the requisite physiologic information for assessing the patient's actual condition can be obtained with only a hemodynamic monitoring system such as HMS 308, i.e., without heart rate monitoring. Thus, the arrangements in FIGS. 3A-3D and their variants and combinations having only HMS 308, HMS 312, or both, (without HRM 306 and/or HRM 310) are all within the spirit of the invention. Alternatively, as described below, certain embodiments of the invention can benefit from heart rate monitoring in addition to, and sometimes in lieu of, hemodynamic monitoring alone.

Figure 4:
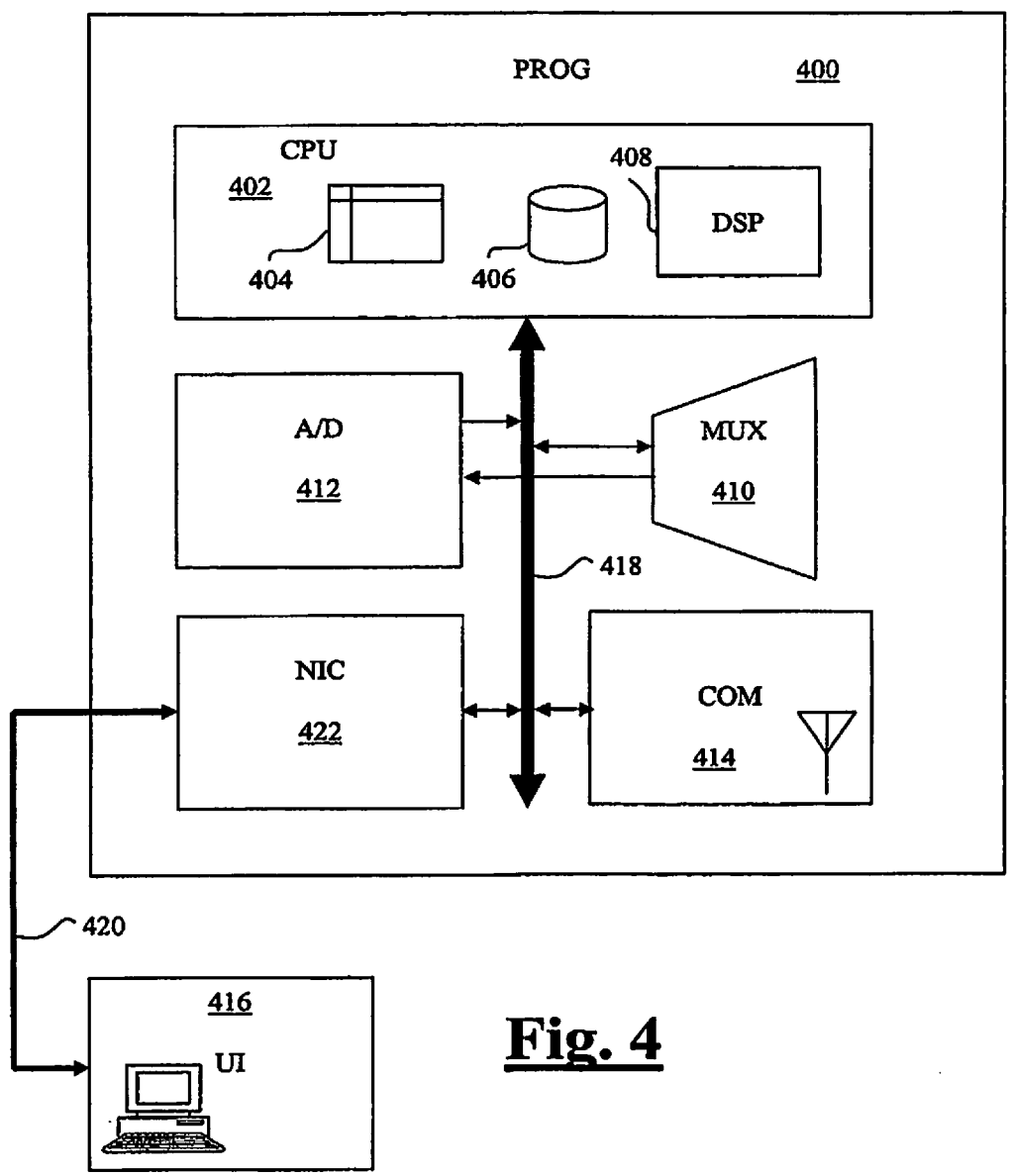
FIG. 4 is a schematic diagram illustrating parts of a programmer according to one embodiment of the invention.

FIG. 4 is a schematic diagram illustrating one embodiment of a programmer 400 for configuring an implanted hypertension treatment device. Programmer 400 can be used with patient monitoring devices or hardware to establish a programming system such as system 100 (FIG. 1) or system 200 (FIG. 2). Programmer 400 can also be used as an embodiment of programmer 304 (FIGS. 3A-3D). Components of programmer 400 include a CPU 402, which includes a processor core such as digital signal processor (DSP) 408, instruction memory space 404, and data storage space 406. In operation, programmer 400 is interfaced with patient monitoring and other equipment via interface multiplexer (MUX) 410. MUX 410 selectively supplies patient monitoring signaling to analog-to-digital converter (AID) 412, which feeds CPU-readable data to CPU 402. MUX 410 can be digitally controlled directly from CPU 402.

Programmer 400 also includes a wireless communications transceiver 414 for facilitating communications with the implanted device. An internal communications bus 418 facilitates data exchange between CPU 402 and the other components of programmer 400. Communications bus 418 can have any suitable bus architecture, as known by persons skilled in the art, including, but not limited to, PCI, SCSI, CAN, I²C, USB, and the like.

As depicted in FIG. 4, programmer 400 is interfaced with a user interface 416. Preferably, user interface 416 is remote from programmer 400. Positioning a clinician operating programmer 400 remotely from the patient during the dose-response testing can realize an advantage by eliminating inadvertent conversations between the clinician and the patient, which are known to adversely impact the accuracy of hemodynamic measurements. To this end, in a preferred embodiment, user interface 416 is communicatively coupled with CPU 402 via interface 420 that is suitable for communications over a relatively larger distance than interface 418. In one such embodiment, interface 420 is an Ethernet or a wireless IEEE 802.11G Wi-Fi-type interface that facilitates operator control of programmer 400 from a remote location, such as a different room. In one embodiment, interface 420 is operatively coupled with bus 418 via network interface controller (NIC) 422.

One aspect of the invention is directed to a method of automatically configuring, or programming, an implanted hypertension treatment device. In one embodiment, the method can be performed without clinician intervention. Optionally, a clinician can monitor the progress of the device configuring process, and intervene if appropriate. One motivation for conducting such programming or configuring is to discover the optimal settings for the implanted hypertension treatment device. In an embodiment in which the implanted device utilizes electrotherapy to regulate blood pressure in the patient, for example, it is desirable for the device to consume a minimal amount of electrical energy to preserve battery life, while ensuring an effective and reliable degree of therapeutic effectiveness, or performance, with a safety margin. According to one type of configuration algorithm, the dose-response testing is conducted such that the therapy dosage administered by the implanted device is incrementally varied according to a predefined sequence, while the effect of the therapy is monitored. The programming system analyzes the results of the tests, and determines the proper settings for various adjustable parameters of the implanted device.

Figure 5A:
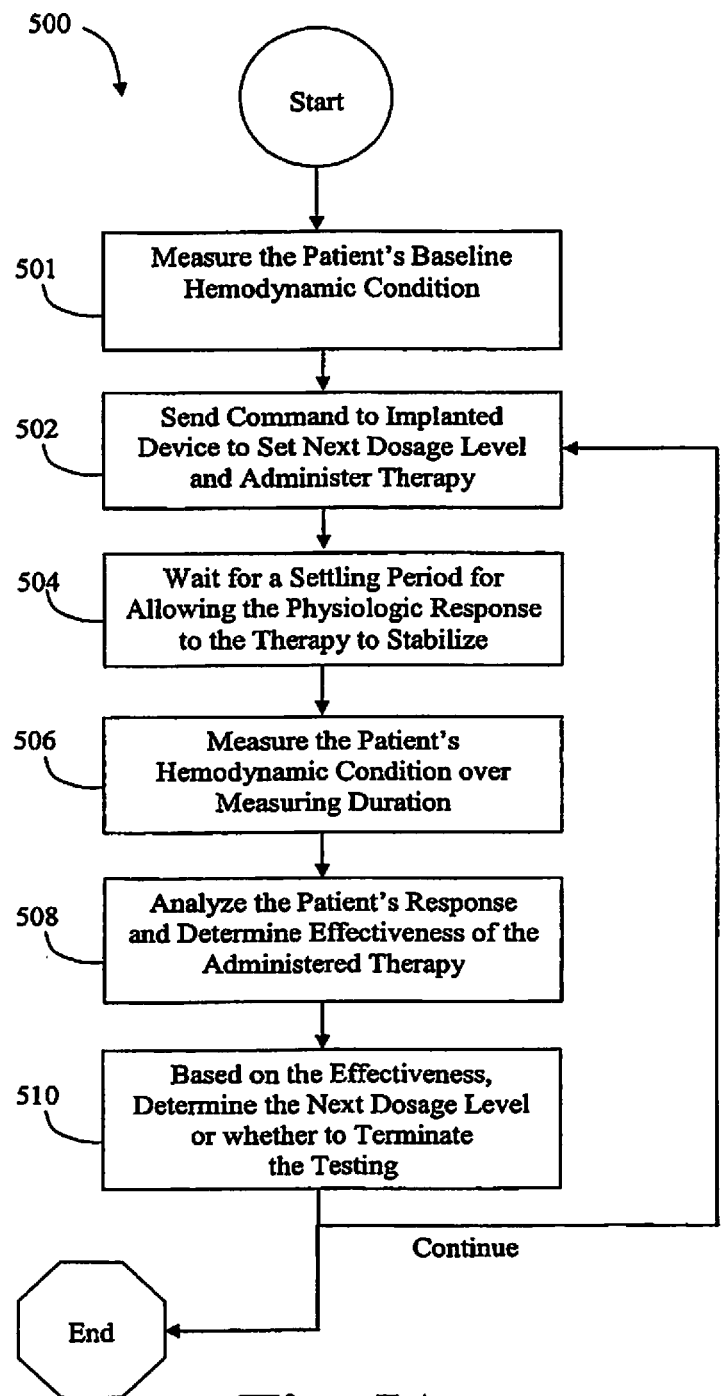
FIGS. 5A-5B are flow diagrams illustrating various methods of configuring an implanted device via dose-response testing.

FIG. 5A illustrates a routine 500 according to one embodiment of the invention for conducting dose-response testing to establish desired settings or configuration of an implanted hypertension treatment device. A programming system, such as system 100 (FIG. 1) or system 200 (FIG. 2) is configured to begin the routine according to a default set of routine parameters, such as initial dosage level, step changes in dosage level, settling time, hemodynamic measurement duration, and hypertension treatment effectiveness assessment criteria. At 501, the programming system measures the patient's baseline hemodynamic condition (i.e., without the administration of therapy by the implanted device). At 502, the system issues a command to the implanted device that instructs the device to administer the first level of therapy. Because the physiologic response of the patient to hypertension therapy may not be immediate, at 504, the system waits for a settling period until the beginning of the measurement window. During this settling period, the hemodynamic measurement in the patient should approach a steady state. Depending on the patient, administered therapy dosage level, type of therapy, type of physiologic monitoring, and other such factors, the settling period can range from several seconds to 5 minutes or more before a reliable measurement can be made for assessing the effectiveness of the administered dosage.

At 506, the system measures the patient's hemodynamic condition over a monitoring time duration. The monitoring time duration can also range from several seconds to 5 minutes or more. In one configuration, the total time between administration of therapy is as little as 15 seconds. In another configuration, the total time is at least a minute. Persons skilled in the art will appreciate that this time can be suitably configured as required to obtain accurate and reliable measurements of the patient's status. Whichever settings are configured for the settling time or measurement period, the automated system is able to consistently and accurately follow the timing protocol for each dose-response test, thereby achieving an improved repeatability over manually-performed measurements. Measurement of the hemodynamic condition includes, but is not limited to, measurement of the patient's pulse rate, systolic pressure, diastolic pressure, mean arterial pressure, pulse pressure, blood oxygenation, electrocardiogram information, cardiovascular resistance, sympathetic/parasympathetic tone, and the like.

At 508, the programming system analyzes the effectiveness of the therapy based on the pre- and post-therapy hemodynamic condition measurements made. The analysis can be further based on a comparison between actual results and expected results. In one embodiment, the programming system will notify the clinician whenever a greater-than-anticipated difference between the actual and expected results is detected. At 510, the system determines whether to continue the dose-response testing. If testing is to continue, the system computes or selects the next therapy dosage for the implanted device to apply, and the process is repeated beginning at 502. Otherwise, if the testing is complete, the system finalizes the programming of the implanted device, and exits from the routine.

Figure 5B:
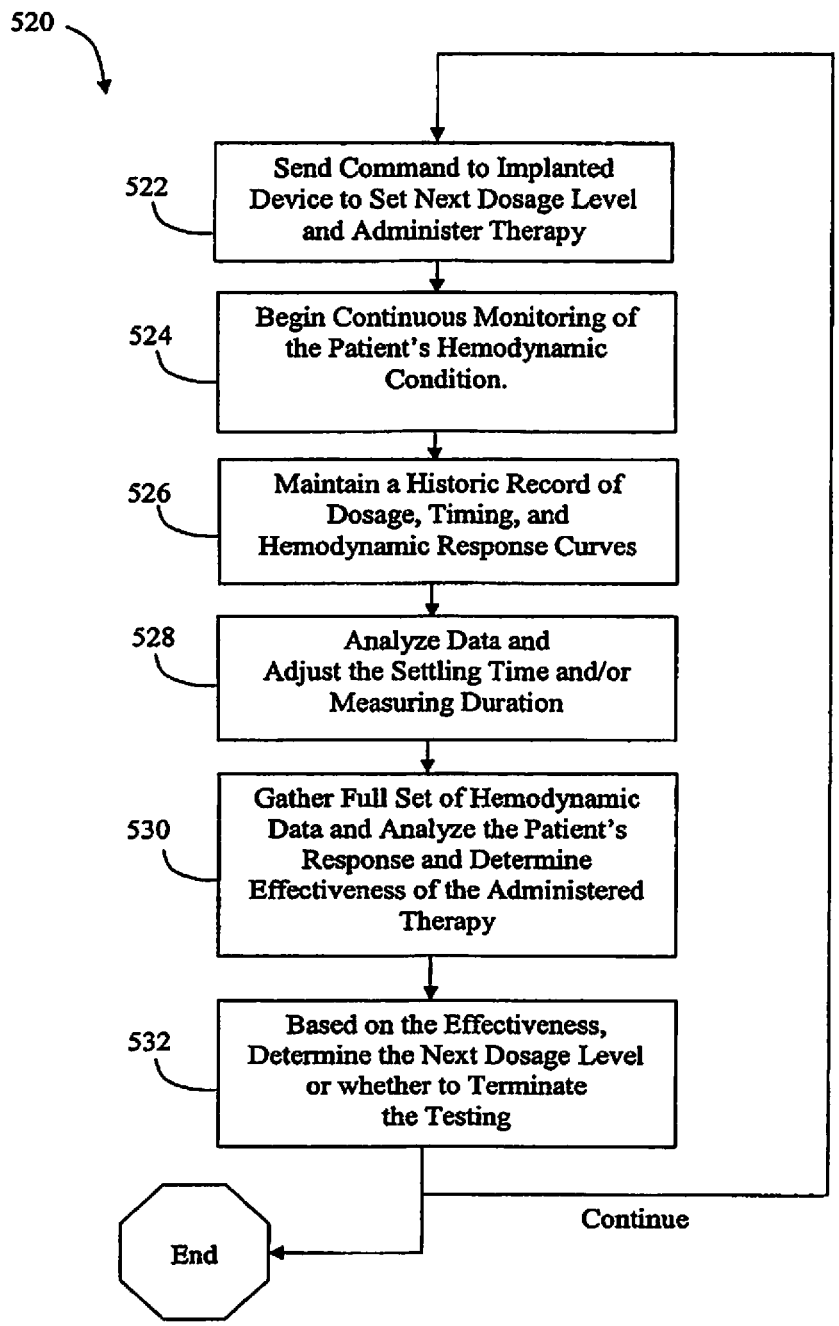

The programming routine illustrated by the flow diagram of FIG. 5B is a variation of method 500 in which the settling time delay and/or the measuring window can be automatically and dynamically adjusted. After instructing the implanted device to administer a selected therapy dose at 522, the programming system begins the monitoring the patient's hemodynamic condition relatively soon (e.g. within several seconds), as indicated at 524. During the monitoring, at 526, the programming system begins building a database of patient condition measurements over time, with dosage and timestamp information included in the records.

Based on the information gathered and analyzed, the system can also dynamically adjust the default measuring duration and settling time while executing a programming routine, as indicated at 528. For example, in a programming system that utilizes both real time (i.e., continuous) and non-real time (i.e., discontinuous) hemodynamic measurements according to one embodiment, the real time measuring begins at 524 immediately after therapy administered. Analyzed real time hemodynamic data as a function of time can indicate an appropriate moment for making a non-real time measurement. Thus, the physiologic settling time delay for the non-real time measurement can be automatically varied for each dose-response test to coincide with the actual time when the patient's condition has stabilized. Persons skilled in the art will recognize that the default measuring duration can be dynamically adjusted in systems where only real time measurement is employed.

As part of the measurement data analysis at 528, the programming system evaluates the shape of the time-based curve generated. This type of analysis permits estimation and/or extrapolation of data, and in one embodiment, is used by the system to shorten the measurement window. For example, if the time rate of change of the patient's monitored blood pressure is not as steep as required for an effective therapy dosage, the system can conclude that a greater dose is needed, and bypass the remaining measurement window, thereby expediting the overall routine. The data collection can also include measurements made over multiple dose-response tests. Thus, data curves can be generated and evaluated to analyze the patient's physiological responsiveness as a function of therapy dosage.

At 530, the system obtains any additional hemodynamic measurements needed to compute the assessment of the effectiveness of the administered therapy. Based on the assessment, at 532, the system determines whether or not to continue the dose-response testing, and which settings to apply to the implanted device in the next loop if testing is to continue.

Figure 6A:
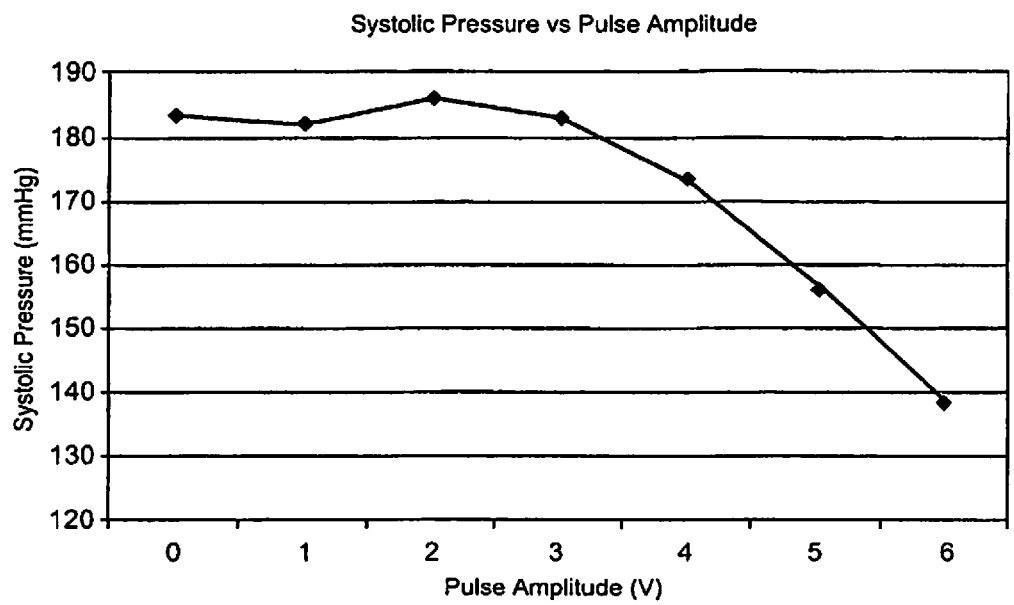
FIGS. 6A and 6B are graphs showing the relationship between systolic blood pressure and heart rate as a function of pulse amplitude for a series of dose-response tests.
Figure 6B:
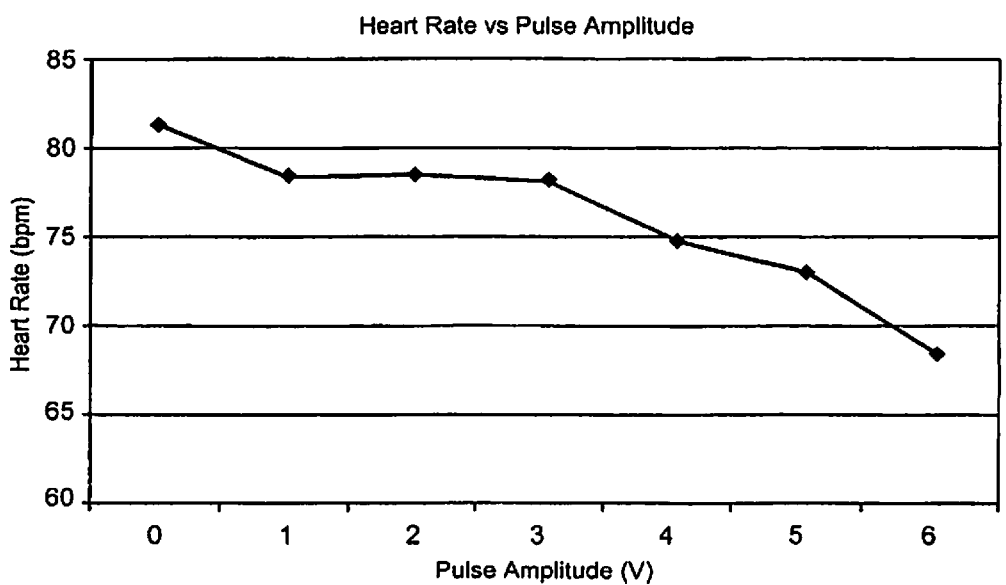

FIGS. 6A and 6B are graphs illustrating an exemplary dose-response in a patient. The curve in FIG. 6A represents measurements of the patient's stabilized systolic blood pressure, while the curve in FIG. 6B represents the measured heart rate of the patient. Both curves are functions of the dosage applied by an electrotherapy device. The graphs of FIGS. 6A and 6B suggests a significant correlation between the heart rate and blood pressure. Based on this physiologic phenomenon, the heart rate measurement, obtainable over a relatively shorter measurement window than the blood pressure measurement, can be used to approximate or predict the patient's blood pressure.

Figure 7:
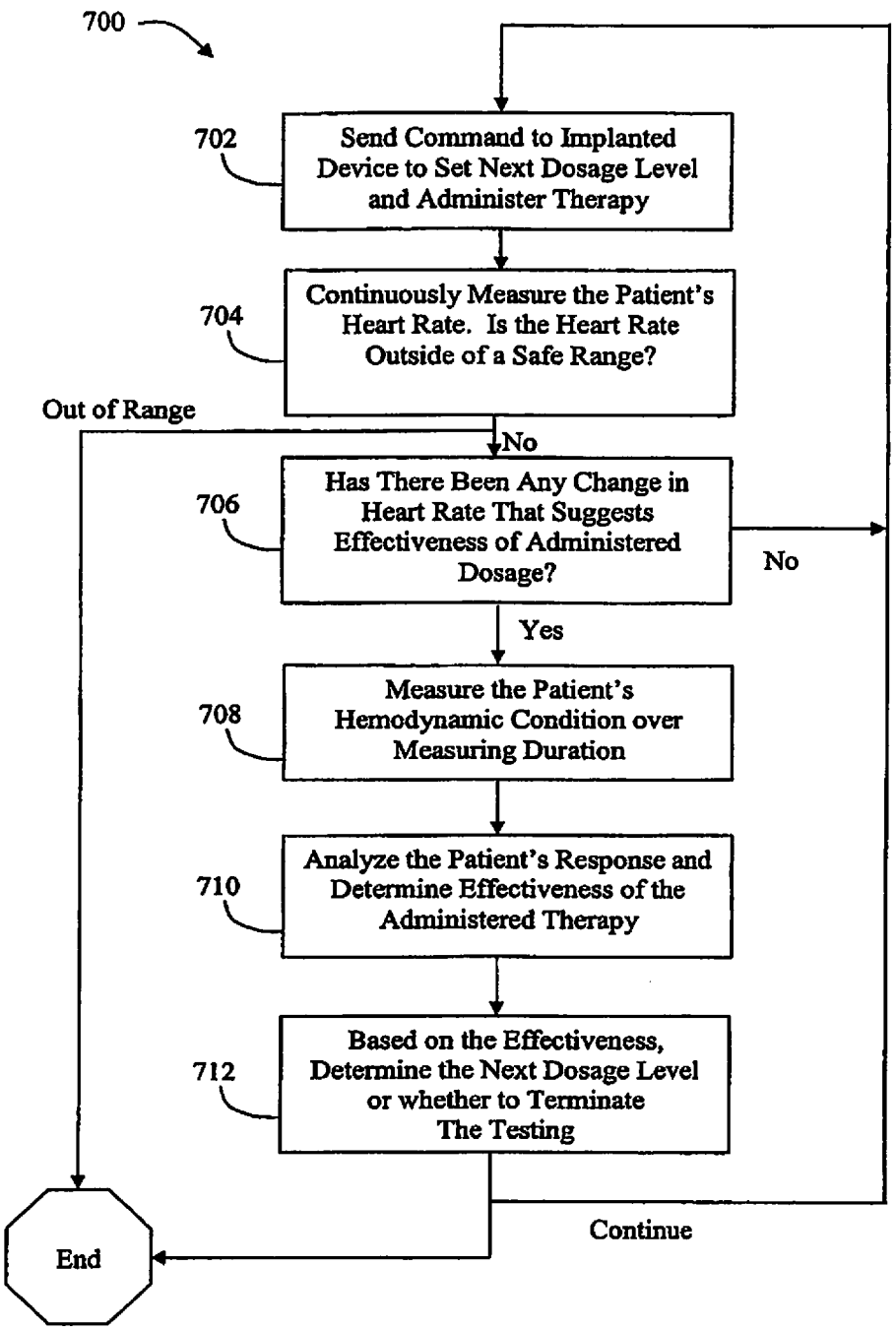
FIG. 7 is a flow chart of one method of quickly predicting effectiveness for each of a plurality of dose-response tests prior to making blood pressure measurements for a given dose-response test.

Taking advantage of the correlation between the heart rate and blood pressure, a method 700 of configuring an implanted device according to one embodiment is illustrated in FIG. 7. At 702, the programming system initiates the dose-response testing and configuring loop by initiating hypertension therapy administration by the implanted device. At 704, soon after the therapy has been administered, the system continuously monitors the patient's heart rate. In one embodiment, the system is configured to automatically test whether the heart rate is within a safe range. If it is outside the safe range, the clinician is notified and the dose-response testing is suspended or terminated either automatically or by the clinician. Related embodiments include measuring or determining one or more other factors representing heartbeat information including, but not limited to, heart rate stability or instability, sympathetic or parasympathetic tone, heart rate variability, and the like.

In another related embodiment, the system processes the heart rate curve as a function of time to predict the time needed for settling of the hemodynamic condition to be measured discontinuously in non-real time. Similarly, one embodiment analyzes the heart rate curve to establish the measuring window for other hemodynamic measurements to follow.

At 706, the programming system processes at least a portion of the collected heart rate information to determine if the administered dosage caused a significant effect on the heart rate. The heart rate analysis can be performed relatively quickly (i.e. on the order of several seconds). If the effect is marginal, the system concludes that the dosage is either too small to have any effect on the patient, or that the most recently administered dosage is not significantly different from the preceding dosage, and returns to 702 to repeat the loop with a different dosage designed to elicit the targeted effect on the patient. In this manner, the system avoids spending time on further hemodynamic monitoring (which could take more than one minute to complete) and analysis of a patient condition that is unlikely to be desirable. If, on the other hand, the effect on the heart rate is measured to be significant, the system will commit to further hemodynamic condition measurement, analysis, and device configuring as indicated at steps 708, 710, and 712.

Figure 8:
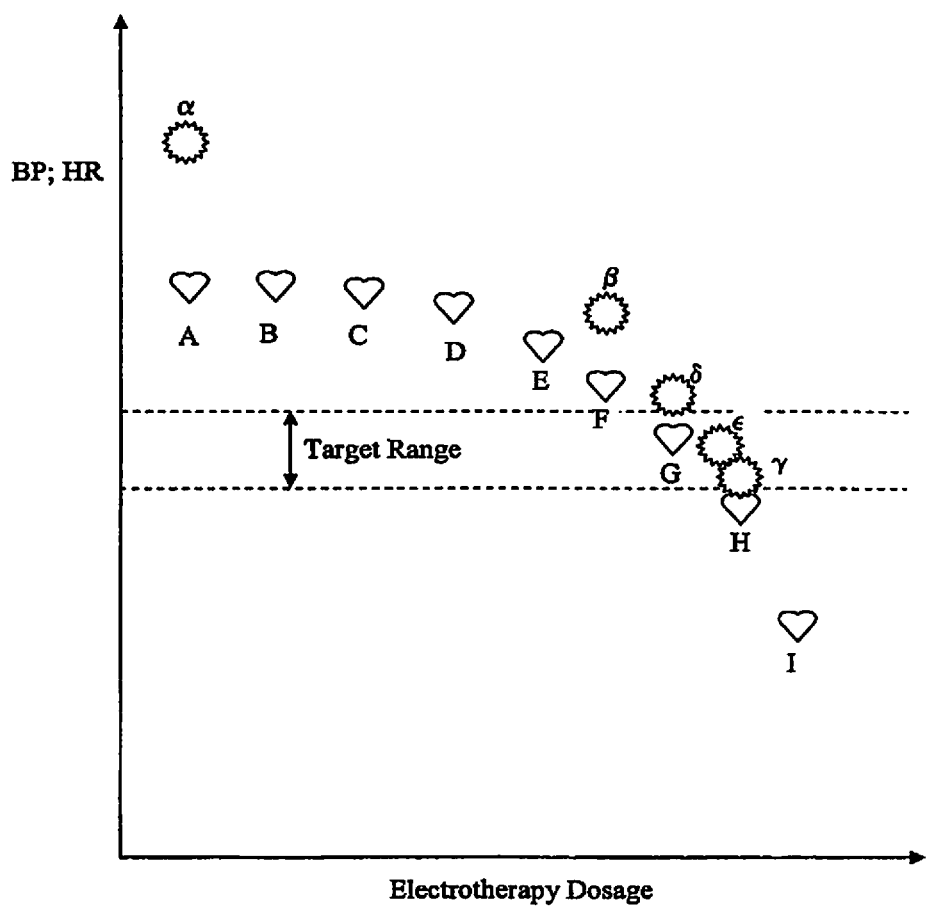
FIG. 8 is a is a diagram illustrating one method of skipping/terminating levels in a series of dose-response tests based on predictive/interpolative analysis of previous dose-response test.

FIG. 8 is a diagram illustrating a method of configuring an implanted electrotherapy-type hypertension treatment device that takes advantage of the correlation between heart rate information and blood pressure, and utilizes interpolative and predictive analysis techniques. In FIG. 8, the vertical axis generally represents the patient's physiologic conditions including heart rate HR and systolic blood pressure BP. The horizontal axis represents the electrotherapy dosage. The Target Range is the desired operating point of the implanted device (i.e. the dosage at which the patient's blood pressure is controlled to be within a desirable range). In one embodiment, the programming system first conducts a series of relatively short-duration dose-response tests, measuring only the patient's heart rate. Reference numerals A-I indicate the result set of the heart rate dose-response measurements at corresponding dosages.

The programming system analyzes data set A-I to assess the general shape of the curve produced as a function of dosage level. Based on certain features of the curve, the programming system determines at which dosage levels to conduct a series of complete hemodynamic measurements. For example, in one embodiment, as illustrated, the first hemodynamic measurement $\alpha$ is conducted at the dosage corresponding to heart rate measurement A. This initial measurement establishes a baseline, relative to which subsequent hemodynamic measurements are planned. The second hemodynamic measurement β is conducted at the dosage corresponding to heart rate measurement F. Heart rate measurement F has been selected according to this exemplary method because it lies at a corner point where the curve slope is approximately −0.5. However, any other suitable criteria for selecting preliminary and subsequent dosage levels is within the spirit of the invention. Because hemodynamic measurement β falls significantly outside and above the Target Range, the programming system selects the dosage corresponding to heart rate measurement H as the third hemodynamic measurement point, producing hemodynamic measurement γ. Measurement γ is only marginally within the Target Range, so the programming system next conducts a hemodynamic measurement at the next lowest dosage corresponding to heart rate measurement G, resulting in hemodynamic measurement δ, which is marginally outside of the Target Range.

Next, the system proceeds to interpolate between the last two hemodynamic measurements δ and γ, favoring a dosage closer to the dosage corresponding to hemodynamic measurement γ because it is closer to the center of the Target Range. The result of the interpolation is hemodynamic measurement ε, which is substantially near the center of the Target Range. The dosage level corresponding to hemodynamic measurement ε is the level for which the system will configure the implanted electrotherapy device. This example method of arriving at the final dosage required only five hemodynamic measurements, compared with eight or nine measurements that would have been made if the programming routine had utilized a simpler incremental approach.

For a more detailed description of one embodiment of a user interface adaptable for use with the present invention, reference is made to "User Interface for Programming/Monitoring Non-Cardiac Tissue Stimulator Devices," Ser. No. 60/584,743, filed Jun. 30, 2004, the disclosure of which is hereby incorporated by reference. For a background reference of implantable devices for treating high blood pressure or hypertension by stimulating various nerves and tissue in the body, reference is made to U.S. Pat. No. 3,650,277 (stimulation of carotid sinus nerve), U.S. Pat. No. 5,707,400 (stimulation of vagal nerve), and U.S. Pat. No. 6,522,926 (stimulation of baroreceptors), the disclosure of each of which is hereby incorporated by reference.

Various modifications to the method may be apparent to one of skill in the art upon reading this disclosure. The above is not contemplated to limit the scope of the present invention, which is limited only by the claims below.

What is claimed is:

1. A system for setting programmable parameters for an implantable baroreflex stimulation device, comprising:
   an implantable baroreflex stimulation device including an electrode configured to be implanted on or in a blood vessel proximate one or more baroreceptors in a wall of the blood vessel; and
   a programming system communicatively interfaced with the implantable baroreflex stimulation device and with a hemodynamic monitoring system configured to collect information representing a hemodynamic response of the patient over a monitoring time duration, the programming system being configured to:
      cause the implantable baroreflex stimulation device to initiate an electrotherapy dose-response test, the test including:
         delivering a plurality of electrotherapy doses of varying levels to the one or more baroreceptors of the patient via the electrode; and
         for each electrotherapy dose, selectively processing the information representing the hemodynamic response of the patient for the monitoring time duration for that electrotherapy dose to establish a patient-specific electrotherapy dose response relationship between the electrotherapy dose and the hemodynamic response of the patient;
      program the implantable baroreflex stimulation device with at least one operating parameter based at least in part on the patient-specific electrotherapy dose-response relationship subsequent to establishing the patient-specific electrotherapy dose-response relationship.

2. The system of claim 1, wherein the programming system is operatively interfaced with a heart rate monitoring system and the programming system is adapted to monitor information representing a heart rate of the patient from the heart rate monitoring system and provide an alert if the heart rate is outside of an expected range.

3. The system of claim 2, wherein the programming system further processes information representing the heart rate of the patient to evaluate effectiveness of the dose-response test.

4. The system of claim 2, wherein the programming system is further adapted to selectively process the information representing the heart rate to evaluate effectiveness of the dose-response test.

5. The system of claim 1, wherein the information representing a hemodynamic response includes at least one hemodynamic information type selected from the set consisting of:
   pulse rate information;
   systolic pressure information;
   diastolic pressure information;
   mean arterial pressure information;
   pulse pressure information;
   oxygenation information;
   electrocardiogram information;
   cardiovascular resistance; and
   sympathetic/parasympathetic tone information.

6. The system of claim 1, wherein the programming system is further configured to set the at least one operating parameter of the implantable baroreflex stimulation device based at least in part on the patient-specific electrotherapy dose-response relationship to achieve a desired performance goal based upon consuming a minimal amount of energy of the implantable baroreflex stimulation device while achieving a desired effect in the patient.

7. The system of claim 1, wherein the programming system is configured to interface with a hemodynamic monitoring system according to an arrangement selected from the set consisting of:
   a separate device in communication with the programmer system, a system incorporated into the programmer system, and a system integrated with the implantable baroreflex stimulation device.

8. The system of claim 1, wherein the programming system further comprises an operator interface that enables a clinician to observe and adjust operation of the system and to provide input utilized to at least alter how the at least one operating parameter is set.

9. The system of claim 8, further comprising data storage memory in operable communication with at least one of the programmer system and the implantable baroreflex stimulation device, the data storage memory configured to store historical data representing the electrotherapy dose-response relationship.

10. The system of claim 1, wherein the programming system is configured to automatically perform the plurality of dose-response tests.

11. A method of establishing programmable parameters for an implantable baroreflex stimulation device in a patient comprising:
providing a programming system that is configured to perform the steps of:
causing the implantable baroreflex stimulation device to initiate an electrotherapy dose-response test, the test including:
delivering a plurality of electrotherapy doses of varying levels to one or more baroreceptors of the patient via an electrode implanted on or in a blood vessel proximate the one or more baroreceptors in a wall of the blood vessel;
monitoring information representing a hemodynamic response of the patient over a monitoring time duration for each of the plurality of electrotherapy doses; and
establishing a patient-specific electrotherapy dose response relationship between the electrotherapy dose and the hemodynamic response;
using the programming system to program the implantable baroreflex stimulation device with at least one operating parameter based at least in part on the patient-specific electrotherapy dose-response relationship subsequent to establishing the patient-specific electrotherapy dose-response relationship.

12. The method of claim 11, further comprising:
monitoring information representing at least a heart rate of the patient over a testing time duration of at least several minutes and providing an alert if the heart rate is outside an expected range.

13. The method of claim 12, wherein the programming system is configured to perform the further step of evaluating the information representing at least the heart rate to determine whether to adjust the monitoring time duration to be greater than or less than a predetermined settling period for assessing a sympathetic nervous response to the electrotherapy dose.

14. The method of claim 13, wherein the step of evaluating the information representing at least the heart rate to determine whether to adjust the monitoring time duration evaluates at least one of a set of factors in the information representing at least the heart rate consisting of heart rate stability, heart rate instability, sympathetic/parasympathetic tone, and heart rate variability.

15. The method of claim 11, wherein the step of using the programming system to set a programmable operating parameter is accomplished by the programming system based on a determination of the effectiveness of the dose-response test to achieve a desired performance goal based upon consuming a minimal amount of energy by the implantable baroreflex stimulation device while achieving a desired degree of therapy plus a safety margin.

16. The method of claim 11, wherein the programming system further comprises an operator interface and wherein the step of using the programmable system to set the at least one operating parameter uses the operator interface to permit a clinician to provide input utilized at least to alter how the at least one operating parameter is set.

17. The method of claim 11, further comprising maintaining a record of previously monitored hemodynamic responses and wherein the step of using the programming system to set a programmable operating parameter of the implantable baroreflex stimulation device is based on the record.

18. The method of claim 11, wherein the information representing a hemodynamic response includes at least one hemodynamic information type selected from the set consisting of:
pulse rate information;
systolic pressure information;
diastolic pressure information;
mean arterial pressure information;
pulse pressure information;
oxygenation information;
electrocardiogram information;
cardiovascular resistance; and
sympathetic/parasympathetic tone information.

19. A method, comprising:
causing an implantable baroreflex stimulation device to be manufactured and made available to a user, the implantable baroreflex stimulation device including an electrode configured to be implanted on or in a blood vessel proximate one or more baroreceptors in a wall of the blood vessel;
causing a programming system to be manufactured and made available to a user, the programming system communicatively interfaced with the implantable baroreflex stimulation device and with a hemodynamic monitoring system configured to collect information representing a hemodynamic response of the patient over a monitoring time duration; and
providing instructions recorded on a tangible medium to the user, the instructions for setting programmable parameters for the implantable baroreflex stimulation device, the instructions comprising:
initiating an electrotherapy dose-response test, the test including:
delivering a plurality of electrotherapy doses of varying levels to the one or more baroreceptors of the patient via the electrode; and
selectively processing the information representing the hemodynamic response of the patient for the monitoring time duration for each electrotherapy dose;
establishing a patient-specific electrotherapy dose response relationship between the electrotherapy dose and the hemodynamic response of the patient; and
programming the implantable baroreflex stimulation device with at least one operating parameter based at least in part on the patient-specific electrotherapy dose-response relationship subsequent to establishing the patient-specific electrotherapy dose-response relationship.

20. A method, comprising:
providing an implantable baroreflex stimulation device to a user, the implantable baroreflex stimulation device including an electrode configured to be implanted on or in a blood vessel proximate one or more baroreceptors in a wall of the blood vessel;
providing a programming system to a user, the programming system communicatively interfaced with the implantable baroreflex stimulation device and with a hemodynamic monitoring system configured to collect information representing a hemodynamic response of the patient over a monitoring time duration; and programming the control system with instructions recorded on a tangible medium for operating the implantable baroreflex stimulation device, the instructions comprising:
  initiating an electrotherapy dose-response test, the test including:
    delivering a plurality of electrotherapy doses of varying levels to the one or more baroreceptors of the patient via the electrode; and
    selectively processing the information representing the hemodynamic response of the patient for the monitoring time duration for each electrotherapy dose;
  establishing a patient-specific electrotherapy dose response relationship between the electrotherapy dose and the hemodynamic response of the patient; and
  programming the implantable baroreflex stimulation device with at least one operating parameter based at least in part on the patient-specific electrotherapy dose-response relationship subsequent to establishing the patient-specific electrotherapy dose-response relationship.

* * * * *